United States Patent
Happonen et al.

(10) Patent No.: US 7,007,798 B2
(45) Date of Patent: Mar. 7, 2006

(54) STORAGE FOR SURGICAL FIXATION DEVICES AND ARRANGEMENT FOR SAME

(75) Inventors: Harri Happonen, Tampere (FI); Andreas Pösel, Tampere (FI)

(73) Assignee: Inion, Ltd., Tampere (FI)

( * ) Notice: Subject to any disclaimer, the term of this patent is extended or adjusted under 35 U.S.C. 154(b) by 289 days.

(21) Appl. No.: 10/147,431

(22) Filed: May 15, 2002

(65) Prior Publication Data

US 2002/0170840 A1   Nov. 21, 2002

(30) Foreign Application Priority Data

May 17, 2001 (FI) ................................. 20011051

(51) Int. Cl.
   *B65D 83/10*   (2006.01)
(52) U.S. Cl. .................. 206/370; 206/339; 606/96
(58) Field of Classification Search ............... 227/136, 227/135; 206/363, 370, 372, 373, 438, 704, 206/338–341; 606/96, 98, 104, 86; 81/121.1, 81/125

See application file for complete search history.

(56) References Cited

U.S. PATENT DOCUMENTS

| | | | |
|---|---|---|---|
| 3,171,408 A * | 3/1965 | Childs et al. ................ 606/96 |
| 4,788,970 A * | 12/1988 | Karas et al. ................ 606/96 |
| 5,015,249 A | 5/1991 | Nakao et al. |
| 5,411,522 A | 5/1995 | Trott |
| 5,437,368 A * | 8/1995 | Mikels ........................ 206/341 |
| 5,445,641 A * | 8/1995 | Frigg et al. .................. 606/96 |
| 5,569,262 A * | 10/1996 | Carney ........................ 606/96 |
| 5,690,639 A | 11/1997 | Lederer et al. |
| 5,938,027 A | 8/1999 | Soroff et al. |
| 6,659,281 B1 * | 12/2003 | Gaffney et al. .............. 206/704 |

FOREIGN PATENT DOCUMENTS

| | | |
|---|---|---|
| FR | 2 785 033 | 4/2000 |
| WO | WO 99/01071 | 1/1999 |
| WO | WO 99/26544 | 6/1999 |
| WO | WO 00/7510 | 2/2000 |
| WO | WO 01/49198 | 7/2001 |

OTHER PUBLICATIONS

English abstract of FR 98 13350.

* cited by examiner

*Primary Examiner*—Luan K. Bui
(74) *Attorney, Agent, or Firm*—Banner & Witcoff, Ltd.

(57) ABSTRACT

A storage for surgical fixation devices and an arrangement for the storage for surgical fixation devices. The storage for fixation devices comprises fixation device slots for at least one fixation device and a guide that is arranged to guide a counter element of an installation tool to a contact section of a fixation device located in the fixation device slot. The arrangement comprises a space for the fixation device storage, to which the storage for fixation devices can be arranged, and a guide for an installation tool, the guide being arranged to guide a counter element of the installation tool to a contact section of a fixation device located in the fixation device slot.

11 Claims, 2 Drawing Sheets

STORAGE FOR SURGICAL FIXATION DEVICES AND ARRANGEMENT FOR SAME

Figure 1A:
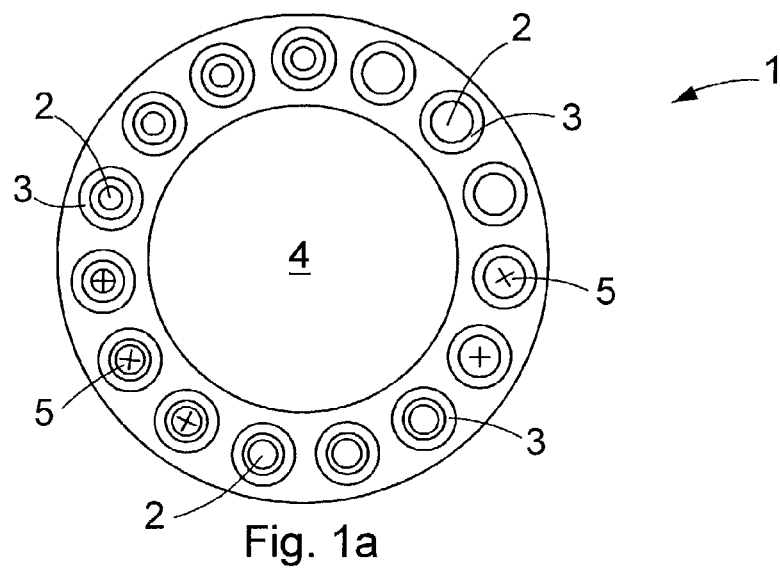

The invention relates to a storage for surgical fixation devices, which storage comprises fixation device slots for at least one fixation device.

The invention further relates to an arrangement for a storage for surgical fixation devices.

In this application, surgical fixation devices refer to all fixation devices that are used to join sections of tissue or to fix implants to tissue. The fixation devices are made of a biostable or biodegradable material. Screws and pins made of biostable materials and materials that dissolve in the organ system, i.e. biodegradable materials, are used in treating fractures, for instance. Implants that support the bone during the healing of a fracture are typically fixed to the bone by means of these fixation devices. The implant keeps the bone in the correct position so as to allow it to heal in the best possible manner.

The fixation devices are fixed to tissue by means of a specific installation tool. For instance, implants are fixed in place by arranging the fixation devices through holes made in the implant and by thereafter fixing the fixation device to tissue.

Screw-type and pin-type fixation devices are known. Screws are fastened by screwing their threads to counter-threads in fixation holes made in tissue. The installation tool of a screw-type fixation device is a manually turned screwdriver, motorized screw twister or a corresponding wrench known per se. Pin-type fixation devices are fixed by pushing the device into tissue—in most cases by shooting it by a pin applicator designed for the purpose. In the following, unless otherwise stated, the term installation tool refers to manual and motorized installation tools for both screw-type and pin-type fixation devices. The fixation devices are usually stored and handled in a specific storage for fixation devices, from which they are, as necessary, picked to the installation tool. In practice, this picking means that the contact section in the head of the fixation device is engaged with a counter-element in the installation tool. The storage for fixation devices has a certain number of fixation device slots, each for holding one fixation device. The fixation devices are either all similar in diameter and length, or the storage for fixation devices comprises a selection of two or more fixation devices having a different diameter and/or length.

A problem is involved in the use of fixation devices. Picking a fixation device from the storage is very difficult and requires high precision, because the fixation devices are very small: their diameters are typically only a few millimeters. Picking is especially difficult when a relatively large and heavy pin applicator or a motorized screw twister is used, but it is also difficult to do with lighter manual installation tools. Naturally, this causes difficulties and loss of time as well as some degree of uncertainty during the operation.

To solve the problem, a pin applicator and a storage for fixation devices connectable thereto are disclosed for handling pin-type fixation devices. The applicator comprises means, by which the fixation device is fed from the storage to the end of the percussion piston of the applicator. After this, the percussion piston shoots the pin into tissue. The solution facilitates the handling of the fixation devices, but makes the structure of the applicator more complex and increases its size and weight. This in turn makes the applicator awkward to handle.

It is an object of the present invention to provide a novel and improved storage for surgical fixation devices and an arrangement for a surgical installation tool.

The storage for surgical fixation devices of the invention is characterized in that the storage also comprises a guide that is arranged to guide a counter element of an installation tool to a contact section of a fixation device located in a fixation device slot.

Further, the arrangement of the invention is characterized in that the arrangement comprises a space to which the storage for fixation devices can be arranged, and a guide for an installation tool, the guide being arranged to guide a counter element of an installation tool to a contact section of a fixation device located in a fixation device slot.

The essential idea of the invention is that the storage for fixation devices comprises a guide that is arranged to guide a counter element of an installation tool to the contact section of the fixation device. Further, the essential idea of a preferred embodiment of the invention is that the guide is arranged to be substantially stationary in relation to the fixation device slot. Further, the essential idea of a second preferred embodiment of the invention is that the guide is arranged to be movable in relation to the frame of the storage for fixation devices in such a manner that the guide is moved to the required fixation device slot. The essential idea of yet a third preferred embodiment of the invention is that the guide is arranged to a guide frame that is detachably attached to the storage for fixation devices.

The invention provides the advantage that due to the guide, picking fixation devices is very reliable and fast. A guide that is arranged stationary in relation to the fixation device slot is always at the correct point and picking can be done immediately. A guide that is arranged movable in relation to the frame of the storage for fixation devices simplifies and lightens the structure of the frame of the storage; in addition, the guide can be designed to be optimal in view of engagement. A guide frame that is detachably attached to the fixation device slot can be moved from one storage to another, whereby the guide frame is maximally utilized.

The invention is described in more detail in the attached drawings, in which

Figure 1B:
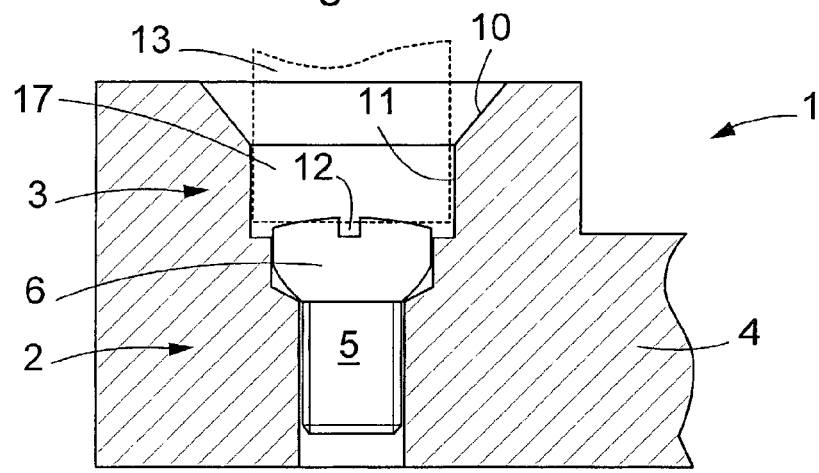
Figure 2:
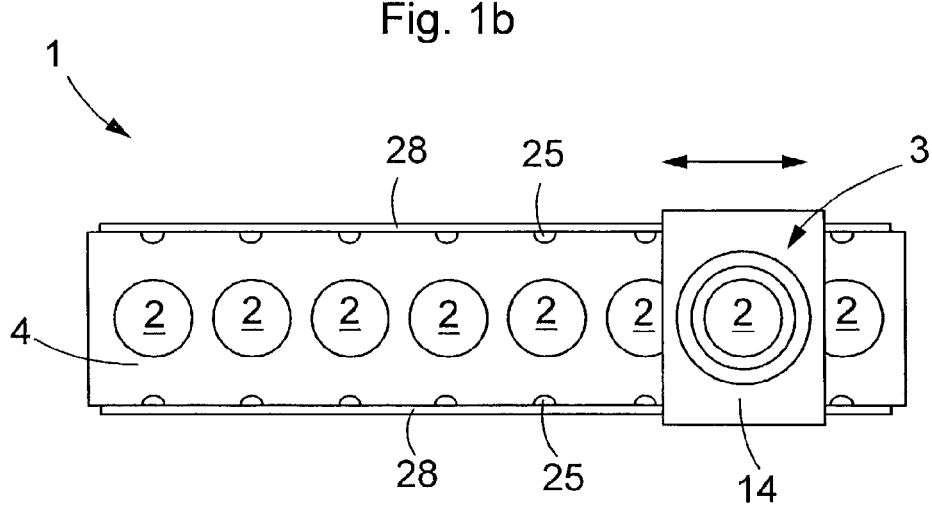
Figure 3A:
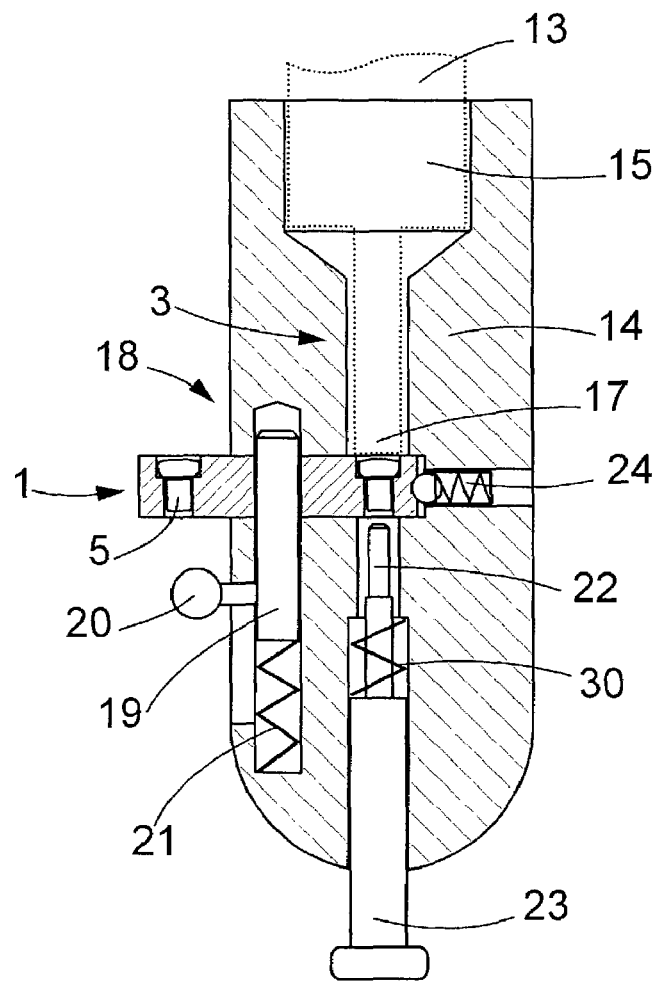
Figure 3B:
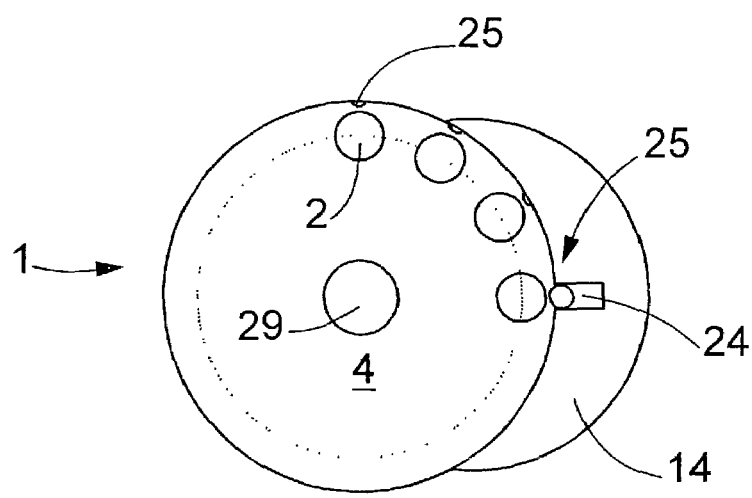

FIG. 1a is a schematic top view of a storage for fixation devices of the invention, FIG. 1b is a partly cross-sectional schematic side view of the storage for fixation devices of FIG. 1a, FIG. 2 is a schematic top view of a second storage for fixation devices of the invention, FIG. 3a is a partly cross-sectional schematic side view of a third storage for fixation devices of the invention and an arrangement of the invention, and FIG. 3b is a partly cross-sectional schematic top view of the storage for fixation devices and arrangement of FIG. 3a.

FIG. 1a is a schematic top view of a storage for fixation devices of the invention, and FIG. 1b is a partly cross-sectional side view of the same. The storage 1 for fixation devices is made of a material approved for medical use that can be sterilized, such as polyoxymethylene (POM), polypropylene (PP), high-density polypropylene (HD-PE), metal, paper-based material or the like. The present storage 1 for fixation devices is a round plate in shape and the fixation device slots 2 are arranged in a circle. The storage 1 for fixation devices has fixation device slots 2 for three fixation devices 5 having different sizes. Fixation devices 5 of different sizes are often needed in an operation and thus it is practical to have fixation devices 5 of different sizes in one and the same storage 1 for fixation devices. The size selection and number of fixation devices 5 in the storage 1 can of course also be other than that shown in the figure; similarly, the storage 1 can be designed to contain fixation devices 5 of only one size. It should be noted that in FIG. 1a, some of the fixation device slots 2 are empty.

The fixation devices 5 are made of a known biodegradable polymer or copolymer material; the manufacturing materials will not, however, be discussed herein in more detail. It should be emphasized that the fixation devices 5 can as well be made of a biostable material. The fixation device 5 shown in FIGS. 1a and 1b is a screw, but it is apparent that it can also be a pin or another type of corresponding fixation device. The head 6 of the fixation device 5 has a contact section 12 for an installation tool 13, more exactly for a counter-element of the installation tool. In the present embodiment, the contact section is made up of crosswise grooves made at the end of the head 6. An installation tool 13 of the crosshead screwdriver-type, for instance, can be arranged in the grooves to fix the fixation device 5 to its fixation point in the tissue. The counter-element of the installation tool 13 and the contact section 12 of the fixation device are dimensioned with each other in such a manner that an interference fit is formed between them, by which the fixation device 5 engages with the installation tool 13. This way, the fixation device 5 can be lifted with the installation tool 13 away from the fixation device slot 2. The fixation device 5 detaches from the installation tool 13 in a suitable manner by pulling, bending or in some other corresponding manner. This engaging the fixation device 5 with the installation tool 13 is known per se. It should be noted that the fixation device 13 is shown by a dashed line in FIG. 1b. It should also be noted that the installation tool 13 can be a manually turned screwdriver, a motorized screw twister or some other corresponding wrench known per se. In addition, the contact section 12 of the fixation device 5 can also be some other wrench element known per se, such as a hex socket, hex head or the like.

The fixation device 5 is locked in its fixation device slot 2 as follows: the upper part 26 of the fixation device slot, which has the head 6 of the fixation device inside it, is dimensioned in such a manner that there is an interference fit between it and the head 6. The lower part 27 of the fixation device slot, which has the fixation parts of the fixation device—in the case of a screw, the thread—inside it, is instead dimensioned to be slightly loose, at least equal in diameter to the threaded part. In other words, the fixation device 5 locks in its fixation device slot 2 only by its head 6.

A guide 3 is arranged to each fixation device slot 2. In the present embodiment of the invention, the guide 3 comprises a conical surface 10 starting from the front surface of the storage 1 for fixation devices and an actual cylindrical guide surface 11 starting at a distance from the front surface. The fixation device 5 is picked from the storage 1 for fixation devices by taking the counter-element 17 of the installation tool 13 to the contact section 12 of the fixation device 5 through the guide 3 first guided by its conical surface 10 and finally by the guide surface 11 and by engaging the counter-element 17 and the contact section 12 with each other by pressing. After this, by pulling the installation tool 13 and possibly by twisting it slightly, the head 6 of the fixation device detaches from the press of the upper part 26 of the fixation device slot and the fixation device, fastened to the installation tool 13, lifts away from the storage 1 for fixation devices. Engaging is very easy, because the guide 3 guides the installation tool 13 in exactly the right position to the contact section of the fixation device 5. The contact sections 12 of different-sized fixation devices 5 are dimensioned alike, whereby the same installation tool 13 can be used to install them all. For the same reason, the dimensions of the guide 3 are the same in each fixation device slot 2. If the size difference between the fixation devices is big or if so desired for some other reason, guides 3 of different sizes can naturally be designed for different-sized fixation device slots 2.

The guides 3 are integrated to the frame 4 of the storage for fixation devices and thus manufactured at the same time with the frame 4. They can also be made as separate components that are later fastened to the frame 4 by gluing, welding or by a snap joint, for instance.

FIG. 2 is a schematic top view of a second storage for fixation devices of the invention. The storage 1 for fixation devices is rectangular and its fixation device slots 2 are arranged linearly with respect to each other. The fixation devices are not shown in FIG. 2 for the sake of simplicity. Contrary to the embodiment shown in FIGS. 1a and 1b, each fixation device slot does not have its own fixed guide 3. Instead, the storage 1 for fixation devices has only one guide 3 that is arranged to a guide frame 14. The guide frame 14 is movably attached to the frame 4 of the storage for fixation devices. The guide frame 14 moves on guide bars 28 arranged at the sides of the frame 4, and the guide bars 28 have guide grooves in the guide frame 14. It should be noted that the guide grooves are not shown in the figure. The frame 4 also has an aligning means 25 for each fixation device slot 2 and the guide frame 14 has a press 24 fitted for the aligning means 25. The press 24 is not shown in FIG. 2, but a corresponding structure is shown in FIG. 3b. The aligning means 25 and press direct the guide frame 14 to exactly the right point in relation to the appropriate fixation device slot 2, whereby engaging the fixation device with the installation tool takes place without problems. Even though the guide 3 is quite large in diameter to facilitate engaging, it has been possible to arrange the fixation device slots 2 tightly next to each other. This way, the capacity of the storage 1 for fixation devices can be maximized. The guide frame 14 can be detachably attached to the frame 4 of the storage for fixation devices, and can thus be moved from one storage 1 to another as necessary.

FIG. 3a is a partly cross-sectional schematic side view of a third storage for fixation devices of the invention and an arrangement of the invention for surgical installation tools, and FIG. 3b is a partly cross-sectional top view of the same. It should be noted that the reference numerals are the same in both figures. The guide frame 14 is substantially cylindrical and made of plastic, plastic composite or metal. The guide frame 14 comprises an installation tool space 15, which is a recess at one end of the guide frame 14. In the figure, an installation tool 13 is arranged in the installation tool space 15. The installation tool 13 is a pin applicator, with which pin-type fixation devices are shot into tissue. The installation tool space 15 is a part of the guide 3. The guide 3 extends to a space 18 for the fixation device storage.

The guide frame 14 further comprises a space 18 for the fixation device storage, to which the storage 1 for fixation devices is arranged. The fixation device slots 2 of the storage 1 for fixation devices extend through the storage from its front surface to the back surface. In addition, the storage 1 for fixation devices comprises at its center a center hole 29. Because a pin applicator is arranged in the installation tool space 15, the fixation devices in the storage 1 for fixation devices are now pin-type devices. It is emphasized that an installation tool 13 intended for screw-type fixation devices can equally well be arranged in the installation tool space 15, in which case the fixation devices 5 in the storage 1 for fixation devices are correspondingly screw-type devices.

The storage 1 for fixation devices and the guide frame 14 are detachably fastened to each other. The fastening is arranged using a longitudinally movable fastening pin 19 that is fitted through the center hole 29 of the storage 1 for fixation devices and dimensioned to fit the center hole with a suitable tolerance. A pull handle 20 is connected to the fastening pin 19 and extends outside the guide frame 14. By pulling the handle 20, the fastening pin 19 can be pulled to its back position to allow the storage 1 for fixation devices to be arranged in the space 18 for the fixation device storage or removed from it. The fastening pin 19 also has a release spring 21 that returns the fastening pin 19 to the position shown in the figure. At the same time, the fastening pin 19 locks the storage 1 for fixation devices arranged in the space 18 for the fixation device storage to the guide frame 14.

The space 18 for the fixation device storage has on the opposing side to the installation tool space 15 a push arm 22 that is coaxial with the guide 3 and arranged movable in the direction of its longitudinal axis in a channel formed in the guide frame 14. A push handle 23 is fastened at one end of the push arm 22, and by pushing the handle, the end of the push arm 22 can be pushed into the fixation device slot 2 of the storage 1 for fixation devices. A second release spring 30 is arranged to the push arm 22 to pull the end of the push arm 22 away from the fixation device slot 2 when the operator allows it.

FIG. 3b shows a press 24 arranged to the guide frame 14 and comprising a ball and a spring that forces the ball towards the space 18 for the fixation device storage, i.e. it is a press-ball structure known per se. An aligning means 25 is made at each fixation device slot 2 on the frame 4 of the storage for fixation devices, the aligning means being simply a recess formed on the outer circumference of the frame, to which the ball of the press 24 fits. By means of the press 24 and aligning means 25, the operator can easily and quickly turn the storage 1 for fixation devices to such a position in the space 18 for the fixation device storage that one of the fixation device slots 2 is exactly at the location of the guide 3 and push arm 22.

The fixation device 5 is taken into use as follows: first the fastening pin 19 is pulled from the space 18 for the fixation device storage with the pull handle 20 and a storage 1 for fixation devices containing the required fixation devices is arranged in the space 18 for the fixation device storage, then the fastening pin 19 is allowed to return to the space 18 for the fixation device storage through the center hole 29 of the fixation device storage. The storage 1 for fixation devices is now turned in relation to the guide frame 14 until the desired fixation device, i.e. the fixation device slot 2, is at the guide 3. If the installation tool 13 is not yet in the guide 3, it is fitted in at this stage. The push arm 22 is pushed into the fixation device slot 2 by using the push handle 23. The push arm 22 pushes the fixation device 5 in front of it against the counter element 17 of the installation tool 13. The fixation device fastens with its contact section 12—that is not shown in FIGS. 3a and 3b but was described in connection with the earlier figures—to the counter element 17. Now the installation tool 13 and the fixation device engaged with the counter element 17 can be pulled out of the guide frame 14. The guide frame 14 facilitates essentially the fitting of the fixation device 5 to the installation tool 13, because the installation tool 13 is always in the correct position in relation to the fixation device to be picked. In addition, the operator gets an excellent grip of the guide frame 14, which further improves the speed and ease of picking.

The guide frame 14 need not necessary have a push arm 22, but in one embodiment of the invention, the length of the guide 3 is arranged such that the counter element 17 of the installation tool is engaged with the contact section of the fixation device simply by pressing the installation tool 13 and guide frame 14 against each other. The storage 1 for fixation devices can be used without the guide frame 14, and for instance a guide frame can be arranged to it that moves in relation to the frame 4, as described in FIG. 2.

The drawings and the related description are intended only to illustrate the idea of the invention. The invention may vary in detail within the scope of the claims. Thus, the guide surfaces 10, 11 of the guide 3 need not necessarily be continuous along the circumference of the guides 3: the guide surfaces 10, 11 can be implemented for instance as, preferably at least three, protruding parts that are substantially parallel to the longitudinal axis of the fixation device slot 2 and arranged at regular intervals on the circumference of the guide 3.

The guide 4 can be designed so that it locks the fixation device 5 to the fixation device slot 2: the free inner diameter of the guide 3 is then smaller than the diameter of the head 6 of said fixation device. The guide 3 is made of an elastic material or its structure is otherwise elastic. When an installation tool 13 bigger than the free inner diameter of the guide 3 is pushed inside it and to the contact section 12 of the fixation device, the guide 3 yields in such a manner that its inner diameter increases and the fixation device 5 fastened to the counter element of the installation tool can be lifted out of the fixation device slot 2. After this, the guide 3 can return to its original dimension without any specific action or its dimensions can be returned by thermal treatment, for instance. The guide that is movably fastened to the frame 4 of the storage for fixation devices can also be implemented together with fixation device slots 2 that are arranged in a circle: The movement of the guide frame is co-centric with the center point of the circle.

The shape of the storage 1 for fixation devices and the placement of the fixation device slots 2 in relation to each other can be other than that shown in the figure. The manufacturing material of the storage 1 for fixation devices can be biodegradable, in which case its disposal after use is trouble-free.

What is claimed is:

1. A storage for surgical fixation devices, which storage comprises fixation device slots for at least one fixation device and a guide having a conical guide surface convergent toward one of the fixation device slots, each fixation device slot positioned beneath the conical guide surface and having an upper portion having a first diameter and a lower portion having a second diameter, the first diameter being larger than the second diameter, wherein the guide is arranged to a guide frame that is fastened movable in relation to a frame of the storage and is arranged to be moved to the required fixation device slot, and an aligning means is arranged to it for aligning the frame of the storage and the guide frame in relation to each other.

2. The storage as claimed in claim 1, wherein the guide is arranged substantially stationary in relation to the fixation device slot.

3. The storage as claimed in claim 2, wherein the guide is arranged in connection with each fixation device slot of the storage for fixation devices.

4. The storage as claimed in claim 1, wherein the guide frame is detachably attached to the storage for fixation devices.

5. The storage as claimed in claim 1, wherein a means for fastening the fixation device to the counter element of the installation tool is arranged to the guide frame.

6. The storage as claimed in claim 5, wherein the means for fastening the fixation device to the counter element of the installation tool is a push arm.

7. The storage as claimed in claim 1, wherein the fixation device slots are arranged circumferentially.

8. The storage as claimed in claim 1, wherein the fixation device slots are arranged substantially linearly in relation to each other.

9. An arrangement for a storage for surgical fixation devices, the arrangement comprising a space in which a storage for fixation devices is arranged having at least one fixation device slot to receive a fixation device, and a guide for an installation tool, the guide having a conical guide surface convergent toward one of the fixation device slots, each fixation device slot positioned beneath the conical guide surface and having an upper portion having a first diameter and a lower portion having a second diameter, the first diameter being larger than the second diameter, wherein an alignment means is arranged to it for aligning a frame of the storage for fixation devices and the guide frame with each other.

10. The arrangement as claimed in claim 9, wherein a means for fastening a fixation device to the counter element of the installation tool is arranged to the guide frame.

11. The arrangement as claimed in claim 10, wherein the means for fastening a fixation device to the counter element of the installation tool is a push arm.

* * * * *